United States Patent
Wu et al.

(10) Patent No.: US 10,398,732 B2
(45) Date of Patent: Sep. 3, 2019

(54) COMPOSITIONS AND METHODS FOR TREATING STRIATED MUSCLE INJURY, TREATING STRIATED MUSCLE ATROPHY AND/OR FOR PROMOTING STRIATED MUSCLE GROWTH

(71) Applicant: Marshall University Research Corporation, Huntington, WV (US)

(72) Inventors: Miaozong Wu, Warrensburg, MO (US); Cuifen Wang, Huntington, WV (US); Eric Blough, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 0 days.

(21) Appl. No.: 15/783,340

(22) Filed: Oct. 13, 2017

(65) Prior Publication Data

US 2018/0104276 A1 Apr. 19, 2018

Related U.S. Application Data

(60) Provisional application No. 62/407,660, filed on Oct. 13, 2016.

(51) Int. Cl.
*A61K 33/30* (2006.01)
*A61K 9/00* (2006.01)
*A61K 45/06* (2006.01)
*A61K 9/10* (2006.01)

(52) U.S. Cl.
CPC ............ *A61K 33/30* (2013.01); *A61K 9/0053* (2013.01); *A61K 9/0095* (2013.01); *A61K 9/10* (2013.01); *A61K 45/06* (2013.01)

(58) Field of Classification Search
None
See application file for complete search history.

(56) References Cited

U.S. PATENT DOCUMENTS

| 8,927,018 B2 | 1/2015 | Laurencin et al. |
| 9,060,932 B2 | 6/2015 | Vol et al. |
| 9,295,718 B2 | 3/2016 | Fraser et al. |
| 9,393,396 B2 | 7/2016 | Peyman |
| 2010/0172994 A1 | 7/2010 | Sigmund et al. |
| 2015/0032044 A9 | 1/2015 | Peyman |

FOREIGN PATENT DOCUMENTS

| CN | 105126125 A | 12/2015 |
| JP | 2015-147733 A | 8/2015 |
| KR | 20150142492 A | 12/2015 |
| MX | 2012015251 A | 6/2014 |
| WO | 2009/050696 A2 | 3/2010 |
| WO | 2011/022350 A1 | 2/2011 |
| WO | 2011/055980 A2 | 5/2011 |
| WO | 2011/106717 A1 | 9/2011 |

OTHER PUBLICATIONS

Powers et al., Muscle injury following experimental intraoperative irradiation, Int J Radiat Oncol Biol Phys. Mar. 1991; 20(3): 463-71, Abstract provided (Year: 1991).*
Focused Ultrasound Foundation, Muscle Atrophy, https://www.fusfoundation.org/diseases-and-conditions/pain-relief/muscle-atrophy , Sep. 5, 2015 (Year: 2015).*
Wu, M., et al. Aging-associated dysfunction of akt/protein kinase B: s-nitrosylation and acetaminophen intervention. PLoS One, 2009. 4(7): p. e6430.
Wu, M., et al. Important roles of Akt/PKB signaling in the aging process. Front Biosci (Sohol Ed), 2010. 2: p. 1169-88.
Liu, H., et al. Regulation of contractile proteins and protein translational signaling in disused muscle. Cell Physiol Biochem, 2012. 30(5): p. 1202-14.
Wang, C., et al. Protective Effects of Cerium Oxide Nanoparticles on MC3T3-E1 Osteoblastic Cells Exposed to X-Ray Irradiation. Cell Physiol Biochem, 2016. 38(4): p. 1510-9.
Andersson, F.I., et al. Backbone assignments of the 26 kDa neuron-specific ubiquitin carboxyl-terminal hydrolase L1 (UCH-L1). Biomol NMR Assign, 2010. 4(1): p. 41-3.
Fishel, M.L., et al. The DNA base excision repair protein Ape1/Ref-1 as a therapeutic and chemopreventive target. Mol Aspects Med, 2007. 28(3-4): p. 375-95.
Hunter, N, et al. Protection by S-2-(3-Aminopropylamino)ethylphosphorothioic Acid against Radiation-induced Leg Contractures in Mice. Cancer Res. 1983;43(4):1630-2.

(Continued)

*Primary Examiner* — Jennifer A Berrios
(74) *Attorney, Agent, or Firm* — Stites & Harbison, PLLC; Terry L. Wright

(57) ABSTRACT

Compositions and methods for treating striated muscle injury, treating striated muscle atrophy, and/or for promoting striated muscle growth are provided and include administering zinc oxide nanoparticles to a subject in need thereof. The zinc oxide nanoparticles can be adminstered before, during, and/or after exposure to an injurious stimuli, such as radiation. Administration of the zinc oxide nanoparticles reduces activation of autophagy regulators, increases striated muscle anabolism, increases DNA repair signaling, and/or increases striated muscle protein synthesis and growth.

14 Claims, 5 Drawing Sheets

(56) References Cited

OTHER PUBLICATIONS

Li, L., et al. Activated cathepsin L is associated with the switch from autophagy to apoptotic death of SH-SY5Y cells exposed to 6-hydroxydopamine. Biochem Biophys Res Commun, 2016.470(3): p. 579-85.

Rai, R., et al. BRIT1 regulates early DNA damage response, chromosomal integrity, and cancer. Cancer Cell, 2006. 10(2): p. 145-57.

Sandri, M. Protein breakdown in muscle wasting: role of autophagy-lysosome and ubiquitin-proteasome. Int J Biochem Cell Biol, 2013. 45(10): p. 2121-9.

Tanida, I., et al. HsAtg4B/HsApg4B/autophagin-1 cleaves the carboxyl termini of three human Atg8 homologues and delipidates microtubule-associated protein light chain 3- and GABAA receptor-associated protein-phospholipid conjugates. J Biol Chem, 2004. 279(35): p. 36268-76.

Wirtz, P., et al. Effects of Irradiation on Regeneration in Dystrophic Mouse Leg Muscles. Br J Exp Pathol. 1982; 63(6):671-9.

Wu J. et al. Molecular cloning and characterization of rat LC3A and LC3B—two novel markers of autophagosome. Biochem Biophys Res Commun, 2006. 339(1): p. 437-42.

Grant, E.J., et al. Risk of death among children of atomic bomb survivors after 62 years of follow-up: a cohort study. Lancet Oncol. 2015; 16(13):1316-23.

Kamiya, K, et al. From Hiroshima and Nagasaki to Fukushima Long-term effects of radiation exposure on health. Lancet 2015; 386(9992):469-78.

Bishit, g., et al. ZnO Nanoparticles: A Promising Anticancer Agent. Nanobiomedicine, 2016.

Watson, C.Y., et al. Effects of zinc oxide nanoparticles on Kupffer cell phagosomal motility, bacterial clearance, and liver function. International Journal of Nanomedicine 2015:1-4173-4184.

Bogutska, K.I., et al. Zinc and zinc nanoparticles: biological role and application in biomedicine. Ukrainica Bioorganica Acta 1 (2013): 9-16.

Hanini, A., et al. Evaluation of iron oxide nanoparticle biocompatibility. Int J Nanomedicine 6 (2011): 787-794.

Yu, K-N, et al. Zinc oxide nanoparticle induced autophagic cell death and mitochondrial damage via reactive oxygen species generation. Toxicology in Vitro 27.4 (2013): 1187-1195.

Rubin, P., et al. Clinical Radiation Pathology as Applied to Curative Radiotherapy. Cancer 1968; 22(4):767-78.

Utley, J.F., et al. Protection of Normal Tissue against Late Radiation Injury by WR-2721. Radiat Res. 1981; 85(2):408-15.

\* cited by examiner

COMPOSITIONS AND METHODS FOR TREATING STRIATED MUSCLE INJURY, TREATING STRIATED MUSCLE ATROPHY AND/OR FOR PROMOTING STRIATED MUSCLE GROWTH

RELATED APPLICATIONS

This application claims priority from U.S. Provisional Patent Application No. 62/407,660, filed Oct. 13, 2016, the entire disclosure of which is incorporated herein by this reference.

GOVERNMENT INTEREST

This invention was made with government support under grant number NNX13AN08A awarded by the National Aeronautical Space Administration. The government has certain rights in the invention.

TECHNICAL FIELD

The presently-disclosed subject matter generally relates to compositions and methods for treating striated muscle injury, treating striated muscle atrophy, and/or for promoting striated muscle growth. In particular, certain embodiments of the presently-disclosed subject matter relate to methods for using zinc oxide nanoparticles to treat striated muscle injury and/or atrophy and for promoting striated muscle growth.

BACKGROUND

The body is comprised of two major muscle types, striated and smooth. Striated muscle is comprised of skeletal and cardiac muscle, while smooth muscle is found mainly in the vascular system and in internal organs. Of these two, striated muscle is the most abundant with skeletal muscle, by itself, comprising up to 40% of a human's body mass. In this regard, it is appreciated that skeletal muscle diseases affect millions of people. The diseases include simple loss of muscle mass, as in disuse, age related, as in sarcopenia, diseases caused by structural defects in the muscle such as in muscular dystrophy, or myopathies caused by certain toxins, drugs, radiation therapy, and inflammatory reactions in the body that are directed against the muscle. Muscle atrophy can result from a co-morbidity of several common diseases and contributing factors from other diseases, including cancer, AIDS, diabetes, obesity, radiation, and many others. A reduced quality of life is often the result of muscle atrophy as the ability to perform some tasks decreases and the risk of falling is increased.

Excessive exposure to DNA damaging agents, such as what is encountered during chemotherapy, space travel, radioactive material operation, medical imaging and radiation exposure, welding, and outdoor work can also cause cellular, tissue, and organ damage, including muscle atrophy and injury. For example, NASA has found that astronauts lose up to 20% of muscle mass on spaceflights for 5 to 11 days. Similarly, cancer patients subject to radiation treatments or some types of chemotherapy drugs experience muscle atrophy and dysfunction. Nevertheless, the effect of exposure to DNA damaging agents, such as ionizing radiation, on muscular injury has not been well studied, and effective strategies to reduce the effects of exposure to such radiation remain limited.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter a method for treating striated muscle injury, such as irradiation-induced striated muscle injury, is provided. In some embodiments, a method for treating irradiation-induced striated muscle injury comprises administering zinc oxide nanoparticles to a subject in need thereof. In some embodiments, the radiation is ionizing radiation. In some embodiments, administering the zinc oxide nanoparticles reduces an amount of striated muscle loss or striated muscle atrophy in the subject. In some embodiments, the striated muscle is skeletal muscle. In some embodiments, the irradiation-induced striated muscle injury is irradiation-induced skeletal muscle atrophy.

With respect to the administration of the zinc oxide nanoparticles, in some embodiments, the administration of the zinc oxide nanoparticles comprises orally administering the zinc oxide nanoparticles. In some embodiments, administration of the zinc oxide nanoparticles comprises administering the zinc nanoparticles before, during, and/or after exposure to an amount of an injurious stimuli, such as radiation. In some embodiments, administering the zinc oxide nanoparticles comprising administering the zinc oxide nanoparticle at a daily dose of about 4 mg/kg per day to about 16 mg/kg per day.

In some embodiments of the presently-disclosed subject matter, administration of the zinc oxide nanoparticles reduces one or more of the symptoms associated with irradiation-induced striated muscle injury. For example, in some embodiments, administering the zinc oxide nanoparticles reduces an amount of activation of an autophagy regulator including, in some embodiments, an autophagy regulator selected from the group consisting of Atg4B, Ubiquitin C-terminal Hydrolase L1 (MA-18), Autophagy Marker Light Chain 3 (LC3A/B), cathepsin-L, and combinations thereof. In other embodiments, administering the zinc oxide nanoparticles attenuates an amount of striated muscle atrophy. In this regard, in some embodiments of the presently-disclosed subject matter, administering the zinc oxide nanoparticles increases an amount of striated muscle mass and/or striated muscle anabolism, such as can be measured by, in some embodiments, an increase in a phosphorylated Akt (pAkt)/total Akt ratio or an increase in an amount of muscle contractile proteins, such as myosin. In further embodiments, administering the zinc oxide nanoparticles increases DNA repair signaling such as by, in some embodiments, increasing an amount of expression of AP endonuclease, BRIT-1, and combinations thereof.

Further provided, in some embodiments of the presently-disclosed subject matter, are methods for treating striated muscle atrophy, including skeletal muscle atrophy. In some embodiments, a method for treating striated muscle atrophy is provided that comprises administering an effective amount of zinc oxide nanoparticles to a subject. In some embodiments, the subject is human or a livestock, such as, in certain embodiments of the methods described herein, a poultry, a fish, a turkey, a beef cattle, a dairy cattle, a pig, a sheep, a goat, a horse, a mule, a donkey, a buffalo, or a camel. In some embodiments, a method of treating striated muscle atrophy is provided that increases an amount of striated muscle mass, increases an amount of striated muscle anabolism, and/or reduces an amount of an autophagy regulator. In some embodiments of the methods of increasing striated muscle atrophy, the striated muscle is skeletal muscle.

Still further provided, in some embodiments of the presently-disclosed subject matter, are methods of promoting striated muscle growth. In some embodiments, a method of promoting striated muscle growth is provided that comprises administering an effective amount of zinc oxide nanoparticles to a subject in need thereof. In some embodiment of the methods of promoting striated muscle growth, the striated muscle is skeletal muscle. In certain embodiments of the methods for promoting striated muscle growth, the subject is a human, a poultry, a fish, a turkey, a beef cattle, a dairy cattle, a pig, a sheep, a goat, a horse, a mule, a donkey, a buffalo, or a camel. In some embodiments, a method of promoting striated muscle growth is provided that increases an amount of striated muscle mass, increases an amount of striated muscle anabolism, and/or reduces an amount of an autophagy regulator.

Further features and advantages of the presently-disclosed subject matter will become evident to those of ordinary skill in the art after a study of the description, figures, and non-limiting examples in this document.

DESCRIPTION OF EXEMPLARY EMBODIMENTS

Figure 1A:
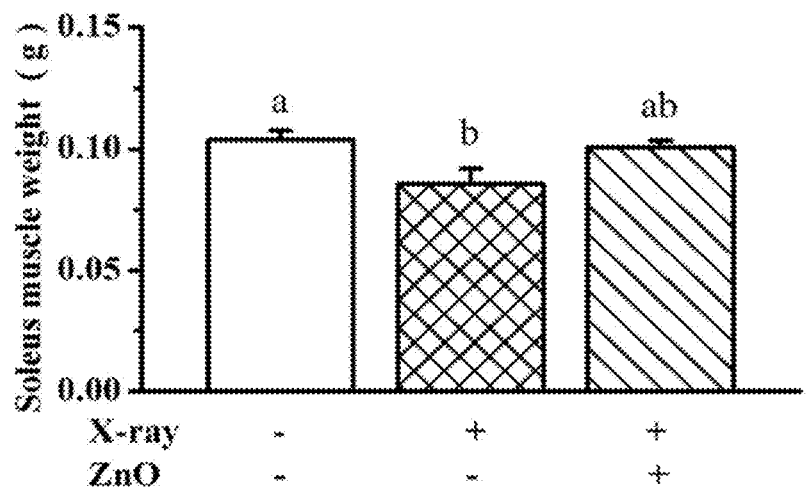
FIG. 1A is a graph showing that X-ray irradiation significantly decreased hindlimb soleus muscle weight, but that hindlimb muscle mass loss as a result of X-ray irradiation was attenuated by zinc oxide (ZnO) nanoparticles (+17%).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended), "consist essentially of," or "consist of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter relates, at least in part, to the discovery that zinc oxide (ZnO) nanoparticles are able to reduce loss of skeletal muscle mass, and diminish skeletal muscle atrophy in skeletal muscle injury. In particular, using an X-ray irradiation induced muscle injury animal model, which can be used to mimic skeletal muscle atrophy caused by space travel and other intentional or unintentional radiation exposures, such as what may occur with chemotherapy, it was discovered that zinc oxide nanoparticles can improve muscle mass by about 17% in irradiated animals. Zinc oxide nanoparticles were also found to significantly improve the abundance of the muscle contractile protein myosin, to improve protein synthesis signaling (phosphorylated Akt (pAkt)/AKT ratio) and DNA repair signaling (AP endonuclease and BRIT-1), and to inhibit an autophagy pathway (Atg4B, Ubiquitin C-terminal Hydrolase L1 (MA-18), Autophagy Marker Light Chain 3 (LC3A/B), and cathepsin-L) in animals exposed to X-ray irradiation. The data, for the first time, thus indicated that zinc oxide nanoparticles can be used to treat striated muscle injury, reduce striated muscle atrophy, stimulate striated muscle growth, and increase striated muscle mass and/or function.

The presently-disclosed subject matter therefore includes compositions and methods for treating striated muscle injury, treating striated muscle atrophy, such as what can occur as a result of skeletal muscle injury, and for promoting striated muscle growth. The phrase "striated muscle injury," as used herein refers to damage or loss in skeletal muscle structure or function. In some embodiments, such striated muscle injury is inclusive of striated muscle atrophy, such as striated muscle atrophy that occurs as a result of: disuse; age; sarcopenia; diseases caused by structural defects in a striated muscle such as in muscular dystrophy; myopathies caused by certain toxins; drugs; radiation therapy; inflammatory reactions in the body of a subject that are directed against striated muscle; and/or as a co-morbidity of several common diseases and contributing factors from other diseases such as cancer, AIDS, diabetes, obesity, radiation, and the like. Additionally, striated muscle injury can, in some embodiments, be characterized by: a reduction of muscle contractile proteins (e.g., myosin) and/or a reduction in muscle contractility; a reduction in protein synthesis signaling and DNA repair signaling; and/or an increase in an autophagy pathway. In some implementations, the striated muscle injury is a skeletal muscle injury, such as skeletal muscle atrophy (e.g., irradiation-induced skeletal muscle atrophy), which refers to a decrease in the mass of the muscle and can include a partial or complete wasting away of muscle.

In some implementations, a method of treating a striated muscle injury and/or promoting striated muscle growth in accordance with the presently-disclosed subject matter includes administering an effective amount of zinc oxide nanoparticles to a subject in need of such a treatment. In some implementations, the striated muscle injury treated through the administration of the effective amount of zinc oxide nanoparticle is an irradiation-induced striated muscle injury. In some embodiments, the radiation producing the injury is ionizing radiation or, in other words, radiation having any amount of energy sufficient to liberate electrons from atoms or molecules and thereby ionize those molecules.

The terms "treatment" or "treating" refer to the medical management of a subject with the intent to cure, ameliorate, stabilize, or prevent a disease, pathological condition, or injury. This term includes active treatment, that is, treatment directed specifically toward the improvement of a disease, pathological condition, or injury, and also includes causal treatment, that is, treatment directed toward removal of the cause of the associated disease, pathological condition, or injury. In addition, this term includes palliative treatment, that is, treatment designed for the relief of symptoms and the promotion of desired outcomes (e.g., meat production) rather than the curing of the disease, pathological condition, or injury; preventative treatment, that is, treatment directed to minimizing or partially or completely inhibiting the development of the associated disease, pathological condition, or injury; and supportive treatment, that is, treatment employed to supplement another therapy directed toward the improvement of the associated disease, pathological condition, or injury.

In some embodiments, the treatment of a striated muscle injury, such as, in certain embodiments, skeletal muscle atrophy can be measured and quantified in several different ways. In some embodiments, treatment can be measured and quantified by, among other things, a reduction in the activation or expression of autophagy regulators in a subject or, in other words, the activation or expression of proteins involved in the degradation and recycling of cellular components (such as what may occur in response to cellular injury as a result of toxin exposure or ionizing radiation exposure), and the promotion of muscle contractile protein synthesis. In some embodiments, the autophagy regulators can be selected from LC3A/B, Atg4B, MA18, cathepsin L, and/or combinations thereof. Alternatively or additionally, in some embodiments, treatment of skeletal muscle injury can be characterized by attenuation of whole body or individual muscle weight, reduced abundance of contractile proteins myosin and actin, increased protein synthesis signaling, and/or increased striated muscle growth and mass. In some embodiments, the treatment of striated muscle injury through the administration of zinc oxide nanoparticles increases an amount of DNA repair signaling including, in certain embodiments, an amount of expression of proteins involved in DNA repair, including, in certain embodiments, AP endonuclease, BRIT-1, and combinations thereof.

As used herein, the terms "reduction" or "reducing" as well as the terms "increase" or "increasing" do not necessarily refer to the ability to completely inactivate or activate all target biological activity in all cases. Rather, the skilled artisan will understand that the terms "reducing" or "increasing" refers to a change in the biological activity of a target. Such decreases and increases in biological activity can be determined relative to a control, wherein the control can be representative of an environment in which, for example, an amount of zinc oxide nanoparticles is not administered. For example, in some embodiments, an increase or decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% increase or decrease.

With still further regard to the various therapeutic methods described herein, although certain embodiments of the methods disclosed herein only call for a qualitative assessment, other embodiments of the methods call for a quantitative assessment. Such quantitative assessments can be made, for example, using known methods, as will be understood by those skilled in the art. Additionally, the skilled artisan will also understand that measuring a reduction or increase in biological activity is a statistical analysis. For example, a reduction in expression or activation of a protein in a subject can be compared to control level of expression or activation (e.g., a level of activation observed in an subject not administered zinc oxide nanoparticles), and an amount of protein activity or expression of less than or equal to the control level can be indicative of a reduction in the activation or expression, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

For administration of a therapeutic composition as disclosed herein (e.g., a therapeutic composition including zinc oxide nanoparticles), in some embodiments of the presently-disclosed subject matter, the composition is administered at a dosage range of about 4 mg/kg/day to about 16 mg/kg/day, such as an average dose of about 7 mg/kg/day. In some embodiments, conventional methods of extrapolating dosage for human or other animal species based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate kg factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery (including in food, drinking water, and as a standalone agent or formulated as an ingredient into an edible product), buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered orally to thereby treat an irradiation-induced skeletal muscle injury.

Regardless of the route of administration, the therapeutic agents used in accordance with the presently-disclosed subject matter are typically administered in an amount effective to achieve the desired response. As such, the term "effective amount" is used herein to refer to an amount of the therapeutic composition sufficient to produce a measurable biological response (e.g., a reduction in striated muscle atrophy or an increase in striated muscle weight and mass). Actual dosage levels of active ingredients in a therapeutic composition used in accordance with the presently-disclosed subject matter can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) *Toxicol. Lett.* 100-101:255-263

With further respect to the administration of zinc oxide nanoparticles in accordance with the presently-disclosed subject matter, in some implementations, the rate of administration of the zinc oxide nanoparticle can be varied. For instance, in some implementations, the administration of the zinc oxide nanoparticles can be in the form of a bolus, optionally with a continuing rate of administration in an amount and at a rate that is therapeutically and/or prophylactically effective. In some embodiments, administration can be continuous or intermittent. In some embodiments, the rate of administration is periodic, such as, for example, daily, twice daily, or hourly.

Additionally, in some implementations of the presently-described methods, an amount of zinc oxide nanoparticles can be administered therapeutically; that is, administered to treat an existing striated muscle injury or condition. In further various aspects, an amount of zinc oxide nanoparticles can be administered prophylactically; that is, administered for reducing the likelihood of a striated muscle injury or condition or for promoting striated muscle growth and increasing muscle weight. Hence, administration can occur prior to the onset of striated muscle atrophy or injury, after onset of striated muscle atrophy or injury, or both before and after the onset of injury. In this regard, in some implementations of the methods of the presently-disclosed subject matter, an amount of zinc oxide nanoparticles can be administered before, during, or after a subject's exposure to radiation. In some implementations, administration of the zinc oxide nanoparticles can then continue for the duration of radiation exposure and/or subsequent to the exposure of the subject to radiation.

With further respect to the methods described herein, in some embodiments, a method for increasing striated muscle growth, including skeletal muscle growth, is provided that comprises administering zinc oxide nanoparticles to a subject. In this regard, in some embodiments, the methods of the presently-disclosed subject matter are particularly beneficial for meat production and use in poultry, fish, and other livestock. In some embodiments, an animal feed is provided that includes an amount of zinc oxide nanoparticles sufficient to protect an irradiation-induced skeletal muscle injury, promote protein synthesis and striated muscle growth (e.g., skeletal muscle growth), and/or increase muscle mass, body weight, and egg production.

The presently-disclosed subject matter further includes and makes use of pharmaceutical compositions comprising the zinc oxide nanoparticles described herein as well as a pharmaceutically-acceptable carrier. Indeed, when referring to certain embodiments herein, the terms "zinc oxide nanoparticle" and/or "composition" may or may not be used to refer to a pharmaceutical composition that includes the zinc oxide nanoparticle. In some embodiments, the zinc oxide nanoparticles utilized in accordance with the presently-disclosed subject matter have an effective particle size of less than 100 nanometers (nm), and, in certain embodiments, have a surface coating to increase the aqueous solubility of the particles and prevent nanoparticle aggregation.

The term "pharmaceutically-acceptable carrier" as used herein refers to sterile aqueous or nonaqueous solutions, dispersions, suspensions, or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants, such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride, and the like.

Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of nanoparticles to biodegradable polymer and the nature of the particular biodegradable polymer employed, the rate of nanoparticles release can be controlled. Depot injectable formulations can also be prepared by entrapping the nanoparticles in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations can further include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents.

The compositions can also take forms such as suspensions, solutions, or emulsions in oily or aqueous vehicles, and can contain formulatory agents such as suspending, stabilizing and/or dispersing agents. Alternatively, the zinc oxide nanoparticles can be in powder form for constitution with a suitable vehicle, e.g., sterile pyrogen-free water, before use.

The formulations can be presented in unit-dose or multi-dose containers, for example sealed ampoules and vials, and can be stored in a condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of tablets or lozenges formulated in a conventional manner.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

With respect to the subjects treated in accordance with the presently-disclosed subject matter, as used herein, the term "subject" includes both human and animal subjects. Thus, veterinary applications are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, fish, and the like. In some embodiments, the subject is a human. In other embodiments, the subject is a poultry, a fish, a turkey, a beef cattle, a dairy cattle, a pig, a sheep, a goat, a horse, a mule, a donkey, a buffalo, or a camel.

The practice of the presently disclosed subject matter can employ, unless otherwise indicated, conventional techniques of cell biology, cell culture, cell growth, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. The examples may include compilations of data that are representative of data gathered at various times during the course of development and experimentation related to the presently-disclosed subject matter.

EXAMPLES

As described in detail below, it was observed that irradiation induced the development of morphological and biochemical changes consistent with skeletal muscle atrophy. Using an X-ray irradiation induced muscle injury animal model, which can be used to mimic skeletal muscle atrophy caused by space travel and other radiation exposures, it was discovered that zinc oxide nanoparticle administration improved muscle mass by 17% in irradiated animals during 21 days of study. The examples show the administration of ZnO nanoparticles markedly attenuated the development of phenotypical features of skeletal muscle atrophy including diminishing skeletal muscle atrophy and increasing skeletal muscle mass measured in the soleus muscle of F344/DuCrl rats.

The following examples thus demonstrate that ZnO nanoparticles can decrease skeletal muscle atrophy and increase skeletal muscle growth and weight in an irradiation induced muscle atrophy mouse model. Molecular signaling changes caused by irradiation were alleviated by ZnO nanoparticle intervention. In particular, the ZnO nanoparticle administration increased the amount of muscle contractile proteins, such as myosin, stimulated skeletal muscle protein synthesis signaling, promoted DNA repair signaling, and reduced the autophagy pathway. The examples show that ZnO nanoparticles reduce several factors indicative of muscle damage, and are potent and effective in improving muscle protein synthesis and preventing muscle weight lost due to ionizing radiation.

Materials and Methods

Experimental designs: Twelve male F344/DuCrl rats (~270-275 grams) were randomly assigned to one of three groups (N=4): age-matched control, and X-ray irradiated vehicle control or daily ZnO nanoparticle (Sigma-Aldrich, St. Louis, Mo.). treatment group (0.1 mg/mL in drinking water). The ZnO nanoparticles utilized were a dispersion of nanoparticles with the nanoparticles having a particle size of less than 100 nm, an average particle size of less than 35 nm, and being about 50 wt % in $H_2O$. Whole body irradiation was performed using a Precision X-RAD 320 irradiator (PXi, North Branford, Conn.) at the dose of 5 Gy each on the day 0, $7^{th}$ and $14^{th}$, respectively. Food and water were provided ad libitum. On day $21^{st}$, soleus muscles were collected from anesthetized rats, weighted, and snap frozen for further analysis. Immunoblotting was performed to detect the target proteins, myosin, pAKT/AKT, AP endonuclease, BRIT-1, LC3A/B, atg4B, MA18, and Cathepsin L using commercially-available antibodies against those proteins. Data were expressed as ±standard error of mean (SEM). One-way ANOVA was used for data analysis when appropriate. The animal study protocol was approved by the Marshall University Institutional Animal Care and Use Committee (IACUC).

Figure 1B:
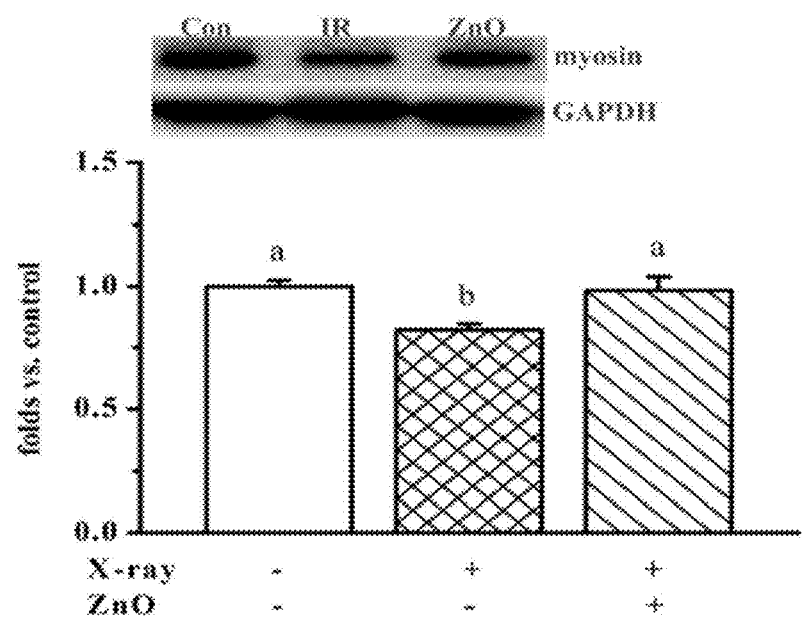
FIG. 1B includes protein blot images and a graph showing that X-ray irradiation significantly decreased muscle myosin protein abundance, but that ZnO nanoparticle administration increased muscle myosin content in irradiated animals, where groups without the same letter are significantly different (a vs. b, $P \leq 0.05$).

Example 1—Zinc Oxide Nanoparticles Reduce Skeletal Muscle Atrophy in a X-Ray Irradiation-Induced Animal Model Skeletal muscle atrophy was explored in an X-ray irradiation induced animal model. FIG. 1A shows X-ray irradiation significantly decreased hindlimb soleus muscle weight, but the muscle mass loss was attenuated by administration of ZnO nanoparticles (+17%). As shown in FIG. 1B, X-ray irradiation significantly decreased muscle myosin abundance, but ZnO nanoparticle treatment increased muscle myosin content in irradiated animals.

Myosin is an important muscle contractile protein that plays essential role in muscle contraction. The increased myosin abundance and skeletal muscle mass indicate that ZnO nanoparticles can be used to treat skeletal muscle loss induced by irradiation, and hence improve skeletal muscle mass and function.

Figure 2:
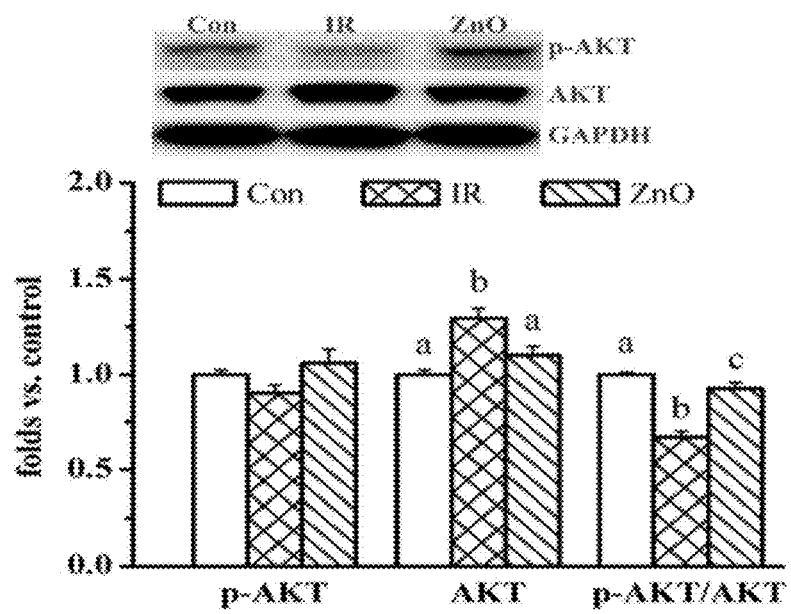
FIG. 2 includes protein blot images and a graph showing that ZnO nanoparticle treatment increased the ratio of phosphorylated Akt (pAkt)/total Akt protein in skeletal muscle in irradiated animals, wherein groups without the same letter are significantly different (a vs. b vs. c, $P \leq 0.05$).

Example 2—Zinc Oxide Nanoparticle Administration Improves Muscle Akt Protein Synthesis Signaling in Animals Exposed to X-Ray Irradiation X-ray irradiation significantly decreased the ratio of phosphorylated Akt (pAkt)/total Akt in skeletal muscle, but, as shown in FIG. 2, ZnO nanoparticle treatment increased the ratio of phosphorylated Akt (pAkt)/total Akt in skeletal muscle in the irradiated animals. The Akt protein is an important protein kinase that plays a central role in stimulating protein synthesis, muscle hypertrophy and cell survival. This finding of increased muscle Akt pathway activation supports that ZnO nanoparticles can improve skeletal muscle anabolism and muscle contractile protein synthesis, and hence prevent skeletal muscle loss induced by irradiation.

Figure 3A:
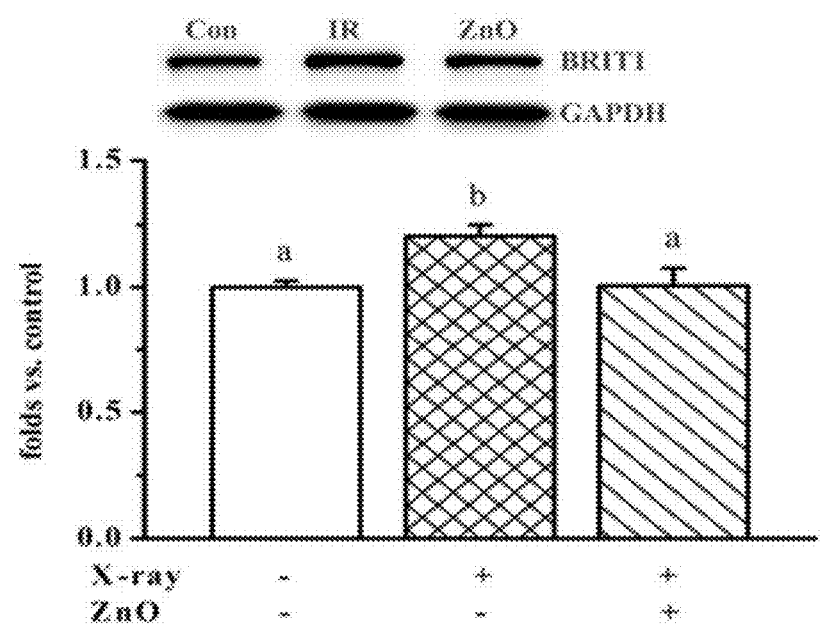
FIG. 3A includes protein blot images and a graph showing the attenuation of BRIT-1 protein abundance after ZnO nanoparticle administration in irradiated animals.
Figure 3B:
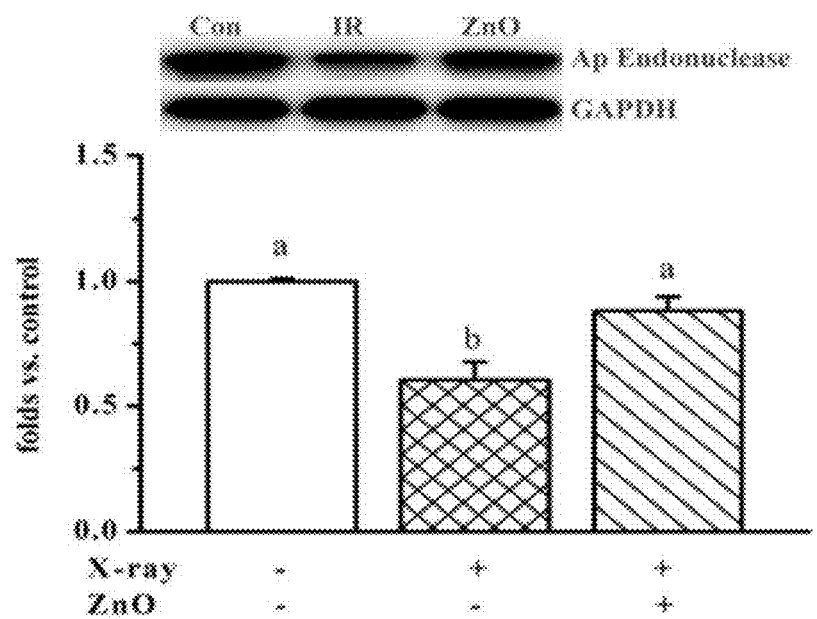
FIG. 3B includes protein blot images and a graph showing X-ray irradiation significantly decreased AP endonuclease protein abundance relative to control, where groups without the same letter are significantly different (a vs. b, $P \leq 0.05$).
Figure 4A:
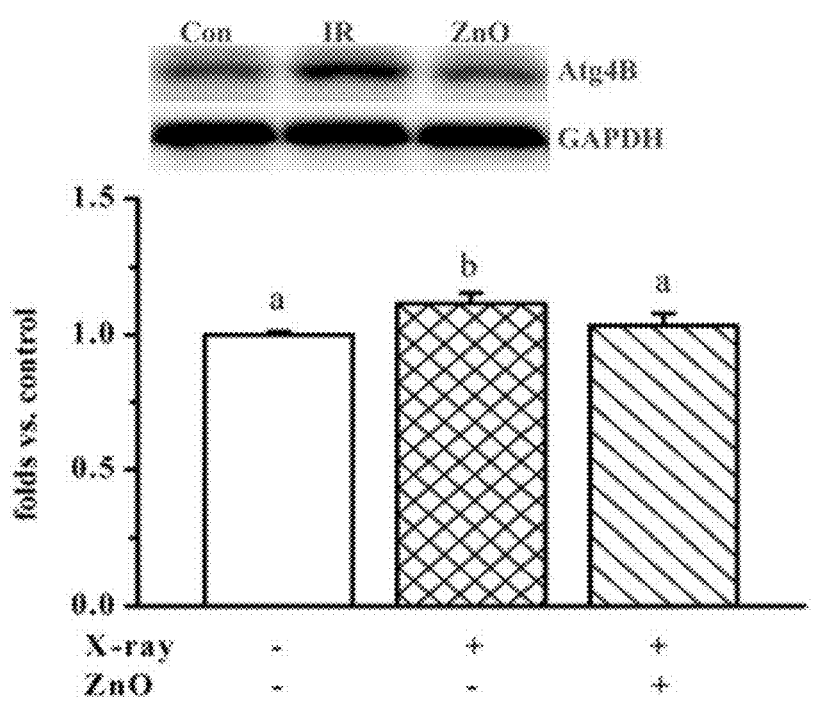
FIGS. 4A-4D include protein blot images and graphs showing irradiation activation of the autophagy pathway, including increase in the abundance of Atg4B protein (FIG. 4A), MA18 protein (FIG. 4B), LC3A/B protein (FIG. 4C), and cathepsin-L protein (FIG. 4D), and further showing a reduction in activation of the autophagy pathway with ZnO nanoparticle administration, where groups without the same letter are significantly different (a vs. b, $P \leq 0.05$).
Figure 4B:
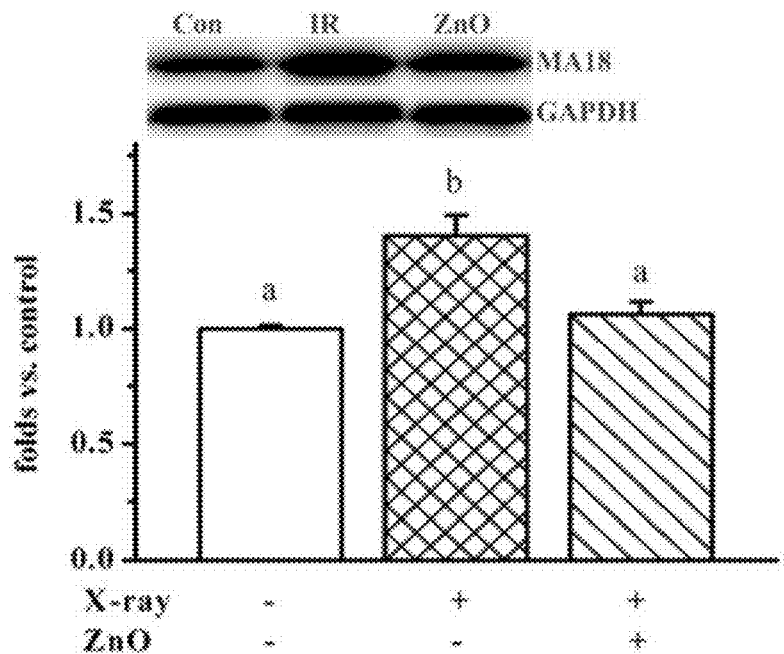
Figure 4C:
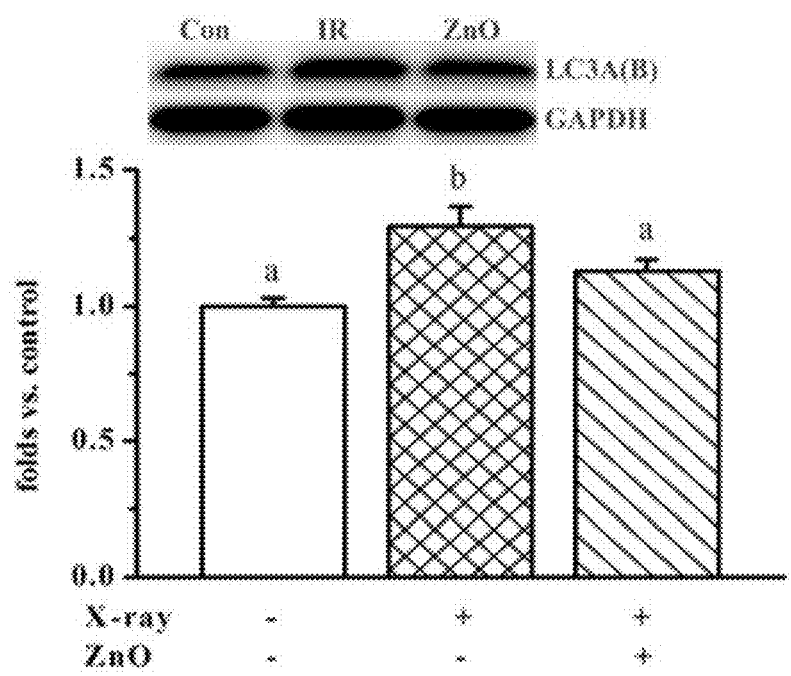
Figure 4D:
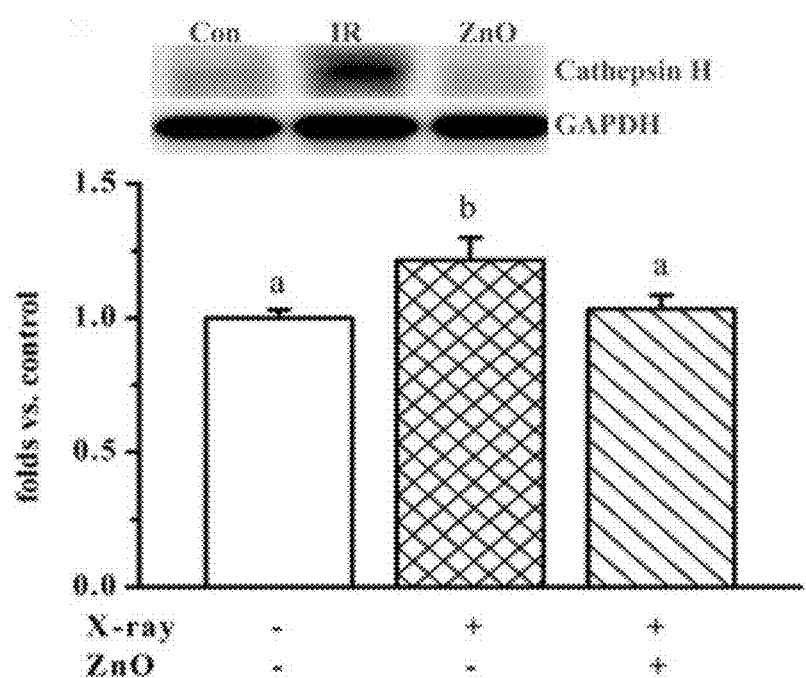

Example 3—Zinc Oxide Nanoparticles Improve Muscle Akt Protein Synthesis Signaling in Animals Exposed to X-Ray Irradiation X-ray irradiation significantly increased BRIT-1 expression, an important DNA damage regulator in response to DNA-damaging stimuli. FIG. 3A illustrates the attenuation of BRIT-1 abundance after ZnO nanoparticle administration. AP endonuclease is a critical enzyme for DNA base excision repair pathway. FIG. 3B shows X-ray irradiation significantly decreased muscle AP endonuclease abundance relative to control. The decrease in muscle AP endonuclease abundance was prevented by ZnO nanoparticle treatment. One deteriorative effect of irradiation is to induce macromolecular damages, particularly DNA. BRIT-1 is an important DNA damage regulator in response to DNA-damaging stimuli, while AP endonuclease is a critical enzyme for DNA base excision repair pathway. The reduction of BRIT-1 and increase of AP endonuclease with administration of ZnO nanoparticles in the irradiation induced muscle atrophy animal model suggest the ZnO nanoparticle is able to increase the DNA repair and hence prevent the deterioration effect of irradiation on skeletal muscle damage.

Example 4—Zinc Oxide Nanoparticles Prevent Skeletal Muscle Autophagy Pathway in X-Ray Irradiation-Induced Animal Model X-ray irradiation significantly increased the abundances of autophagy-related factors (Atg4B, Ubiquitin C-terminal Hydrolase L1 (MA-18), Autophagy Marker Light Chain 3 (LC3A/B), and cathepsin-L) in skeletal muscle. Autophagy is a catabolic process in which bulk cytoplasmic contents are degraded, and plays a critical role in skeletal muscle atrophy. A group of autophagy-related factors, including Atg4B, MA18, LC3A/B, and cathepsin-L have been shown to exert important functions in induction and maintenance of autophagy process. ZnO nanoparticle treatment was able to prevent the activation of those autophagy regulators. As shown in FIGS. 4A-4D, irradiation activates the autophagy pathway, with an increase in the abundance of Atg4B (FIG. 4A), MA18 (FIG. 4B), LC3A/B (FIG. 4C), and cathepsin-L (FIG. 4D), but ZnO nanoparticle treatment can suppress the process. The data further supports ZnO nanoparticle's protective role in reducing muscle atrophy and damage.

Discussion

In the foregoing experiments, exposure to X-rays induces DNA damage and autophagy, impairs DNA repair and protein synthesis signaling, and reduces muscle contractile protein content and skeletal muscle mass. X-ray irradiation also significantly decreased body weight and individual muscle weight, but the muscle mass loss was attenuated by ZnO nanoparticles (+17%). Irradiation significantly reduced the abundance of contractile protein myosin in soleus muscle, inhibited protein synthesis signaling (pAKT/AKT ratio) and DNA repair signaling (AP endonuclease and BRIT-1), but elevated the autophagy pathway (LC3A/B, atg4B, MA18 and cathepsin L). In parallel with the attenuated muscle mass loss, these molecular signaling changes were alleviated by ZnO nanoparticle intervention. Oral administration of ZnO nanoparticles, for example, the equivalent to 10 mg/kg/d, can attenuate irradiation-induced muscular injuries at both molecular and tissue levels.

Throughout this document, various references are mentioned. All such references are incorporated herein by reference, including the references set forth in the following list:

REFERENCES

1. Wu, M., A. Katta, M. K. Gadde, H. Liu, S. K. Kakarla, J. Fannin, S. Paturi, R. K. Arvapalli, K. M. Rice, Y. Wang, and E. R. Blough, Aging-associated dysfunction of akt/protein kinase B: s-nitrosylation and acetaminophen intervention. PLoS One, 2009. 4(7): p. e6430.
2. Liu, H., E. R. Blough, R. Arvapalli, Y. Wang, P. J. Reiser, S. Paturi, A. Katta, R. Harris, N. Nepal, and M. Wu, Regulation of contractile proteins and protein translational signaling in disused muscle. Cell Physiol Biochem, 2012. 30(5): p. 1202-14.
3. Wu, M., B. Wang, J. Fei, N. Santanam, and E. R. Blough, Important roles of Akt/PKB signaling in the aging process. Front Biosci (Schol Ed), 2010. 2: p. 1169-88.
4. Wang, C., E. Blough, X. Dai, O. Olajide, H. Driscoll, J. W. Leidy, M. July, W. E. Triest, and M. Wu, Protective Effects of Cerium Oxide Nanoparticles on MC3T3-E1 Osteoblastic Cells Exposed to X-Ray Irradiation. Cell Physiol Biochem, 2016. 38(4): p. 1510-9.
5. Rai, R., H. Dai, A. S. Multani, K. Li, K. Chin, J. Gray, J. P. Lahad, J. Liang, G. B. Mills, F. Meric-Bernstam, and S. Y. Lin, BRIT1 regulates early DNA damage response, chromosomal integrity, and cancer. Cancer Cell, 2006. 10(2): p. 145-57.
6. Fishel, M. L. and M. R. Kelley, The DNA base excision repair protein Ape1/Ref-1 as a therapeutic and chemopreventive target. Mol Aspects Med, 2007. 28(3-4): p. 375-95.
7. Sandri, M., Protein breakdown in muscle wasting: role of autophagy-lysosome and ubiquitin-proteasome. Int J Biochem Cell Biol, 2013. 45(10): p. 2121-9.
8. Li, L., L. Gao, Y. Song, Z. H. Qin, and Z. Liang, Activated cathepsin L is associated with the switch from autophagy to apoptotic death of SH-SY5Y cells exposed to 6-hydroxydopamine. Biochem Biophys Res Commun, 2016. 470(3): p. 579-85.
9. Tanida, I., Y. S. Sou, J. Ezaki, N. Minematsu-Ikeguchi, T. Ueno, and E. Kominami, HsAtg4B/HsApg4B/autophagin-1 cleaves the carboxyl termini of three human Atg8 homologues and delipidates microtubule-associated protein light chain 3- and GABAA receptor-associated protein-phospholipid conjugates. J Biol Chem, 2004. 279 (35): p. 36268-76.
10. Andersson, F. I., S. E. Jackson, and S. T. Hsu, Backbone assignments of the 26 kDa neuron-specific ubiquitin carboxyl-terminal hydrolase L1 (UCH-L1). Biomol NMR Assign, 2010. 4(1): p. 41-3.
11. Wu, J., Y. Dang, W. Su, C. Liu, H. Ma, Y. Shan, Y. Pei, B. Wan, J. Guo, and L. Yu, Molecular cloning and characterization of rat LC3A and LC3B—two novel markers of autophagosome. Biochem Biophys Res Commun, 2006. 339(1): p. 437-42.
12. Kamiya K, et al. Lancet 2015; 386(9992):469-78.
13. Grant E J, et al. Lancet Oncol. 2015; 16(13):1316-23.
14. Rubin P, et al. Cancer 1968; 22(4):767-78.
15. Wirtz P, et al. Br J Exp Pathol. 1982; 63(6):671-9.
16. Utley J F, et al. Radiat Res. 1981; 85(2):408-15.
17. Hunter N and Milas L. Cancer Res. 1983; 43(4):1630-2.

It will be understood that various details of the presently disclosed subject matter can be changed without departing from the scope of the subject matter disclosed herein. Furthermore, the description provided herein is for the purpose of illustration only, and not for the purpose of limitation.

What is claimed is:

1. A method for attenuating or decreasing irradiation-induced striated muscle atrophy, comprising administering zinc oxide nanoparticles to a subject in need thereof.

2. The method of claim 1, wherein the striated muscle is skeletal muscle.

3. The method of claim 1, wherein administering the zinc oxide nanoparticles comprises orally or parenterally administering the zinc oxide nanoparticles.

4. The method of claim 1, wherein administering the zinc oxide nanoparticles comprises administering the zinc nanoparticles before, during, and/or after exposure to an amount of radiation.

5. The method of claim 4, wherein the radiation is ionizing radiation.

6. The method of claim 1, wherein administering the zinc oxide nanoparticles reduces an amount of activation of an autophagy regulator.

7. The method of claim 6, wherein the autophagy regulator is selected from the group consisting of Atg4B, Ubiquitin C-terminal Hydrolase L1 (MA-18), Autophagy Marker Light Chain 3 (LC3A/B), cathepsin-L, and combinations thereof.

8. The method of claim 1, wherein administering the zinc oxide nanoparticle increases an amount of striated muscle anabolism.

9. The method of claim 8, wherein the increase in skeletal muscle anabolism is measured by an increase in a phosphorylated Akt (pAkt)/total Akt ratio or an increase in an amount of muscle contractile proteins.

10. The method of claim 1, wherein administering the zinc oxide nanoparticles increases DNA repair signaling.

11. The method of claim 10, wherein administering the zinc oxide nanoparticles increases an amount of expression of AP endonuclease, BRIT-1, or combinations thereof.

12. The method of claim 1, wherein the subject is selected from the group consisting of a human, a poultry, a fish, a turkey, a beef cattle, a dairy cattle, a pig, a sheep, a goat, a horse, a mule, a donkey, a buffalo, Of and a camel.

13. The method of claim 1, wherein administering the zinc oxide nanoparticles increases an amount of striated muscle mass.

14. The method of claim 1, wherein administering the zinc oxide nanoparticles comprising administering the zinc oxide nanoparticle at a daily dose of about 4 mg/kg to about 16 mg/kg.

* * * * *

UNITED STATES PATENT AND TRADEMARK OFFICE
CERTIFICATE OF CORRECTION

PATENT NO. : 10,398,732 B2
APPLICATION NO. : 15/783340
DATED : September 3, 2019
INVENTOR(S) : Miaozong Wu, Cuifen Wang and Eric Blough It is certified that error appears in the above-identified patent and that said Letters Patent is hereby corrected as shown below:

In the Claims

Claim 12, Column 16, Line 28, replace "buffalo, Of and a camel." with "buffalo, and a camel."

Signed and Sealed this
Fifteenth Day of October, 2019

Andrei Iancu
*Director of the United States Patent and Trademark Office*